United States Patent [19]

Schäfer et al.

[11] Patent Number: 5,800,547
[45] Date of Patent: Sep. 1, 1998

[54] VENTRAL INTERVERTEBRAL IMPLANT

[75] Inventors: Bernd Schäfer; Stephan Schmitz, both of Schorndorf, Germany

[73] Assignee: Schafer micomed GmbH, Schorndorf, Germany

[21] Appl. No.: 736,437

[22] Filed: Oct. 24, 1996

Related U.S. Application Data

[63] Continuation of Ser. No. 394,017, Feb. 23, 1995, abandoned.

[30] Foreign Application Priority Data

Aug. 20, 1994 [DE] Germany .......... 94 13 471 U

[51] Int. Cl.⁶ .......... A61F 2/44
[52] U.S. Cl. .......... 623/17
[58] Field of Search .......... 623/17; 606/61, 606/63, 68

[56] References Cited

U.S. PATENT DOCUMENTS

| | | | |
|---|---|---|---|
| 16,151 | 12/1856 | Stone et al. | 408/178 |
| 817,042 | 4/1906 | Burns | 408/178 |
| 2,685,877 | 8/1954 | Dobelle | 606/68 X |
| 4,237,875 | 12/1980 | Termanini | 606/63 |
| 4,599,086 | 7/1986 | Doty | 623/17 |
| 4,636,217 | 1/1987 | Ogilvie et al. | 623/17 X |
| 4,892,545 | 1/1990 | Day et al. | 623/17 |

FOREIGN PATENT DOCUMENTS

| | | | |
|---|---|---|---|
| 1225561 | 4/1986 | U.S.S.R. | 606/61 |
| 1424826 | 9/1988 | U.S.S.R. | 623/17 |
| 8707134 | 12/1987 | WIPO | 606/61 |
| 9000037 | 1/1990 | WIPO | 606/61 |

*Primary Examiner*—David H. Willse
*Attorney, Agent, or Firm*—Jones, Tullar & Cooper, P.C.

[57] ABSTRACT

A ventral intervertebral implant is used between two vertebral bodies of a spinal column. The implant has an upper and a lower contact surface and at least one anchor pin projecting beyond at least one of the contact surfaces. An instrument is provided for engagement with the implant and which extends as many anchor pins as are provided relative to the contact surfaces. The instrument is removable from the implant.

24 Claims, 3 Drawing Sheets

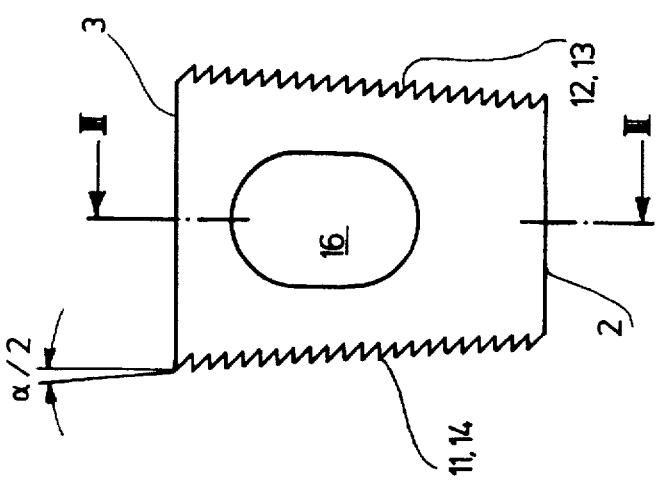
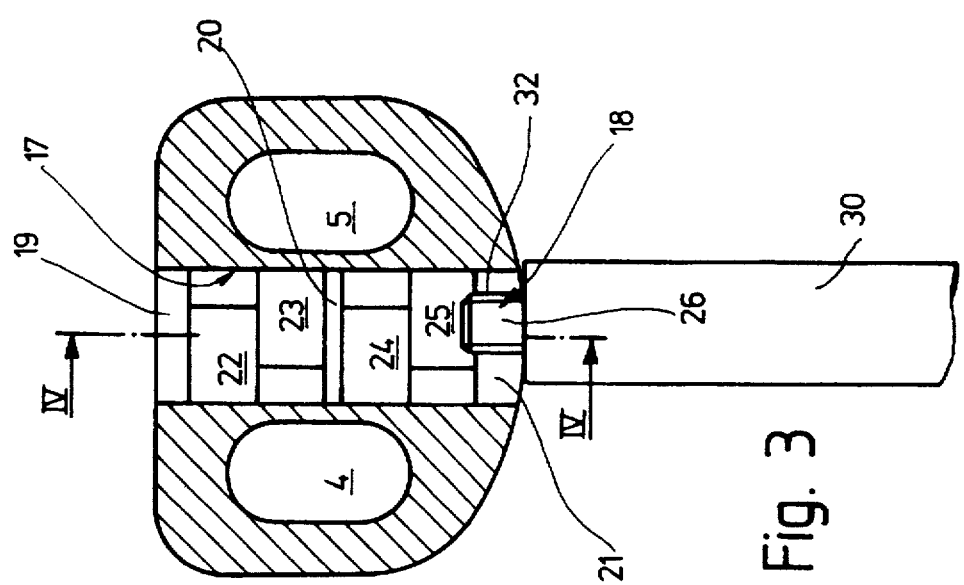
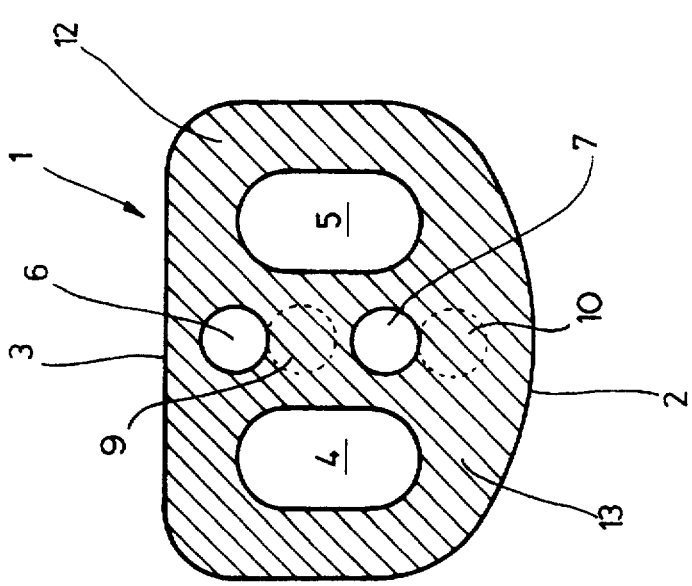
Fig. 2
Fig. 3
Fig. 1

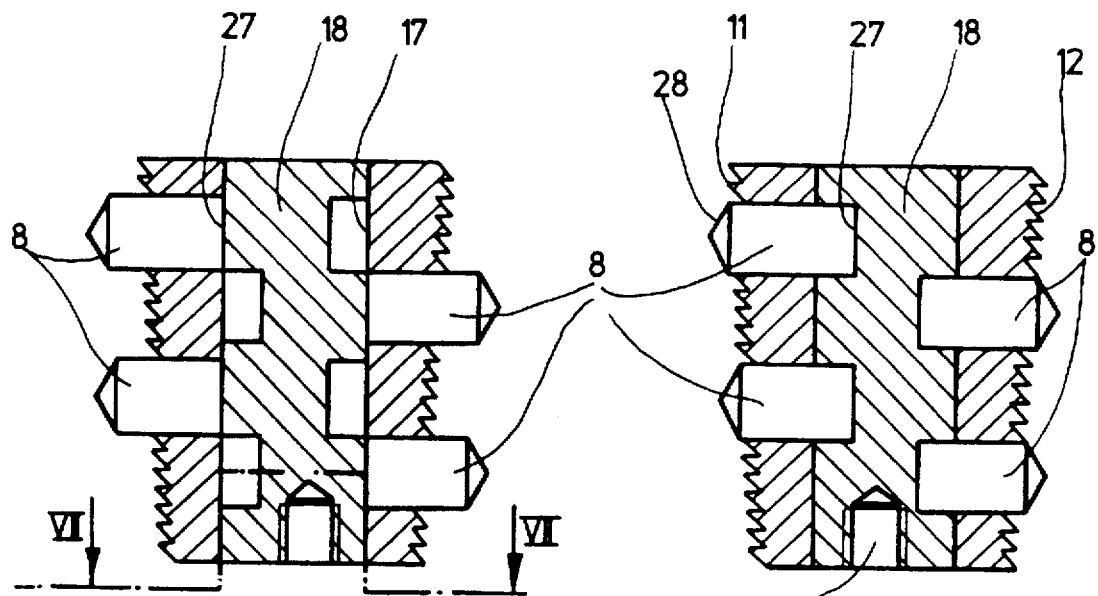
Fig. 5    Fig. 4
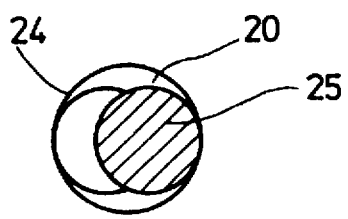
Fig. 7    Fig. 6

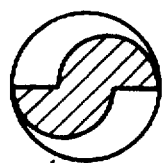
Fig. 9 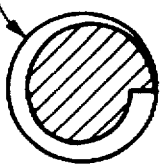    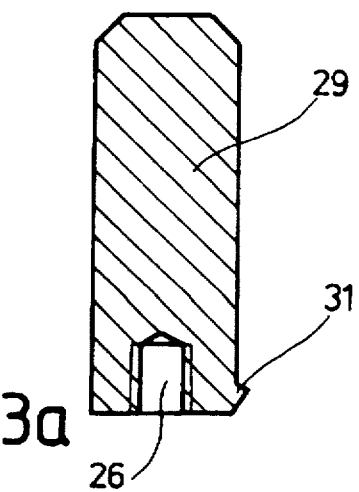 Fig. 3a

VENTRAL INTERVERTEBRAL IMPLANT

This is a continuation of application Ser. No. 08/394,017 filed on Feb. 23, 1995, now abandoned.

FIELD OF THE INVENTION

The present invention relates to a ventral intervertebral implant for use between two vertebrae of a spinal column, for instance, having an upper and a lower contact surface and at least one anchor pin projecting from at least one contact surface, wherein the at least one anchor pin is disposed to be retractable and the implant has a gear for extending the anchor bolt.

BACKGROUND OF THE INVENTION

The individual vertebrae of the spinal column have a vertebral body, a vertebral arch, a vertebral spine, a transverse process, and two upper and lower articular processes. The vertebrae are connected via intervertebral disks (disci intervertebralis) resting against their vertebral bodies (corpus vertebrae). These intervertebral disks comprise fluid-rich fibrous cartilage, and they connect the individual vertebral bodies to one another. The size of the intervertebral disks increases from top to bottom to correspond to the stress occurring in the human body. The intervertebral disks serve as flexible cushions, and resiliently damp impacts. It is known that the intervertebral disks can become dislocated, or that the inside gelatinous core nucleus pulposus can slip out through tears in the connective-tissue-like, fibrous outer ring (annulus fibrosis). In such a case, the intervertebral disk can partly intrude into the intervertebral holes (foramina intervertebralia) or into the spinal canal. Moreover, this prolapse can be medial, dorsomedial or lateral. Prolapses of these types occur most frequently at the $L_4$–$L_5$, $L_5$–$S_1$ and $C_6$–$C_7$ vertebrae. If such prolapses are not treated with therapy, irreversible pressure damage to nerve roots or transverse lesions can result. Should symptomatic physiotherapy, such as physical therapy or massage, not appear promising, the discus intervertebralis must be surgically removed. This presents the option of implanting an artificial intervertebral disk, or osteosynthesis of the two vertebrae via a rigid intervertebral implant.

An artificial intervertebral disk is known from European Patent Disclosure 392 076 A1 that comprises an upper and a lower contact surface and a flexible intermediate layer. Anchor pins, via which the artificial intervertebral disk is secured to the vertebral bodies, project from the contact surface. It has been found to be disadvantageous that this known artificial intervertebral disk can only be inserted with difficulty between the two vertebral bodies, because the anchor pins hamper insertion.

A rigid intervertebral implant that is likewise inserted between two vertebral bodies for osteosynthesis is known from U.S. Pat. No. 5,192,327. The two contact surfaces of this implant are provided with V-shaped longitudinal grooves intended to be used to fix this implant to the vertebral bodies. It has been shown that, notably in the first twelve to sixteen weeks after implantation, the implant slips particularly easily, because at this time the fixation via the V-shaped grooves is not sufficient. Connective tissue only grows gradually into the openings of the implant, thus fixing the implant to the vertebral body.

An artificial intervertebral disk is known from International Patent Application WO 90/00037 which published has anchor bolts projecting beyond the seating face. However, the individual anchor bolts of this intervertebral disk must be pivotably seated, wherein the pivot arm must have a defined length. No anchor bolts can be provided in the area of this pivot arm. Therefore the number of anchor bolts is limited to a small number. Furthermore, in the course of the extension, the anchor bolts travel over an arc of a circle, which is possibly not desired. Therefore an optimum fix is not always assured.

OBJECT AND SUMMARY OF THE INVENTION

Therefore, an object of the present invention is to make available an intervertebral implant with the design described at the outset and that, on the one hand, is to be simply inserted, for example ventrally or dorsally, between the vertebral bodies, and can optimally be fixed to them and furthermore adds in lowering the costs.

This object is attained in accordance with the present invention in that the at least one anchor pin is disposed to be retracted, that the implant has a gear for extending the anchor pin and that the gear is an instrument or a part of an instrument.

By means of the retractable arrangement of the anchor pin(s), when the anchor pin(s) is (are) retracted, the implant can be pushed in between the two vertebral bodies without problems, that is, the spacing between the two vertebral bodies need not be larger than the height of the implant. Along with the simpler placement, the present invention also has the advantage that, after removal of the intervertebral disk, the two vertebral bodies do not have to be forced wider apart in order to insert the implant, which could result in injury to the articular surfaces. As a rule, the spacing of the vertebral bodies is identical prior to and following the operation, or it corresponds to the spacing that would be present with a healthy intervertebral disk.

In order to fixate the implant with the vertebral bodies after the implant has been positioned, the anchor pins are pushed out of the retracted position by means of a gear and penetrate into the vertebral bodies. By means of this, an optimum primary fixation of the implant is achieved, so that immobilization of the patient can be terminated a short time after the operation. The primary fixation by means of the extended anchor pins also has the advantage that the implant and the vertebral bodies resting against it cannot execute movements relative to each other and, because of this, the connective tissue can penetrate into the implant immediately after the operation. This significantly accelerates the healing process.

In accordance with the present invention, the gear is embodied as an instrument and is removed from the implant after the anchor bolts have been pushed out into their work position in which they project past the surface(s) of the implant. This has the decisive advantage that the gear can be employed several times, which considerably contributes to cost reduction. As will be explained in more detail hereinbelow, such gears are very expensive to make, for which reason a one time only use is not justified.

In one exemplary embodiment, the gear has an axial threaded bore, into which a journal of a manually operable instrument rod can be turned.

In an advantageous manner, the anchor bolts are locked in their work position after having been pushed beyond the gear. In a further development it is provided that this locking can be released again. The anchor bolts can furthermore be retracted again via the gear. This gear can be inserted dorsally or ventrally into the implant. The implant has appropriate openings or a through-opening for this.

In one embodiment, the gear has a wedge that pushes out the anchor pin(s). In another exemplary embodiment, the gear has a rotatably seated cam that pushes out the anchor pin. In this gear, the moving and force directions are diverted in the direction of the anchor pin. In the process, the anchor pin can be pushed out of its retracted position through corresponding recesses in the contact surfaces by means of a displacement or turning movement, for example, and pushed into the vertebral body.

Preferably a plurality of anchor pins can be pushed out via one or a plurality of cams. In this way a plurality of anchor pins can simultaneously be brought from their resting position into the operating position, and can penetrate into one or both vertebral bodies.

It is provided in a further development that the one cam or a plurality of cams is or are disposed on one or a plurality of shafts. In larger implants in particular, such as implants for the vertebrae lumbales of the lumbar spine region, it is advisable to dispose anchor pins operated by means of two shafts in at least two planes. One shaft, by means of which the anchor pins can be pushed out in one plane, is sufficient for the vertebrae cervicales of the cervical spine region, e.g. for the region of the $C_1-C_7$ vertebrae.

The shaft is preferably seated in a bore provided between the contact surfaces. Seats of this type are simple to produce and completely receive the entire shaft. In this case, the bore can be disposed in such a manner that the shaft is accessible ventrally, dorsally or laterally.

Simple handling of the shaft is attained in that it can be moved by means of a tool and has an interior thread or a corresponding tool application surface. An interior thread is preferred because by means of it the camshaft can be simply connected with the tool, or different shafts can be connected with the tool.

In a preferred embodiment, the shaft is embodied in the manner of a camshaft, with a plurality of cams disposed axially one behind the other. When a shaft of this type is rotated around its axis, the anchor pins are pushed out via the cams, either simultaneously or in sequence. The advantage of simultaneous ejection is that the cams can be provided with a very long regulating distance, whereas a sequential ejection has the advantage that only the required number of anchor pins can be pushed out in a directed manner.

A disk-shaped collar that respectively projects radially beyond the cams is preferably provided between the cams or between a plurality of cams. Because the anchor pins rest on the cam with their proximal face end, the radially projecting collars prevent the shaft from being pulled out of the bore, because the collars rest laterally against the anchor pins.

In this case, each collar advantageously forms a seating position for the shaft. Correspondingly, the surface of each collar can be treated such that either low friction is attained for easy adjustment or twisting of the shaft, or high friction is attained to insure against the shaft twisting on its own.

In an exemplary embodiment the regulating distance of the cam extends over 180° or 360°. With a regulating distance of 360°, the entire controlling force is distributed over one complete rotation of the shaft. With a regulating distance of 180°, anchor pins can be provided on opposite sides that can then be extended simultaneously by means of a half-rotation of the shaft. In this instance, a cam can be provided with two regulating distances extending over respectively 180°.

If the shaft has only one direction of rotation, the shaft can be provided with a rotational stop. By means of this stop, operating errors are avoided, particularly an overrotation of the shaft.

In accordance with a preferred exemplary embodiment, the anchor pins have a cylindrical cross-section and are seated in corresponding recesses in the implant. The anchor pins can be embodied as circular-cylindrical pins with a distal point, for example, that rest on the cam with their proximal, flat ends.

An optimum conformity of the implant to the shape of the intervertebral disks is attained in that the implant is embodied to be wedge-shaped, and the two contact surfaces form a wedge angle of 2 to 15, particularly 3 to 10 degrees. Most notably in the region of the $C_1-C_7$ vertebrae, which assume a lordosis position, the position of the vertebrae to be connected to one another via the implant is maintained. The same applies for the vertebrae lumbales, where the vertebrae likewise assume a lordosis position. With the vertebrae thoracales, the individual vertebrae assume a kyphotic position, so that implants with a wedge angle rotated by 180° can be used here.

The thickness of the implant also corresponds to the respective point of insertion, that is, thinner implants are used with the vertebrae cervicales than with the vertebrae lumbales. In addition to a surface for the primary fixation, for long-term fixation implant has at least one contact surface that has a profiled surface provided in particular with saw toothing. By means of the saw toothing, the implant can be secured against unilaterally-acting displacement forces. In an advantageous manner, both contact surfaces have saw toothings that block in different directions: for instance, the one blocks ventrally, and the other blocks dorsally. Implants embodied in this manner are particularly unsusceptible to displacement forces, for instance to being pushed in further in the dorsal direction or being pushed out in the ventral direction.

Further advantages, features and details ensue from the following description, in which particularly preferred exemplary embodiments are represented in detail with reference to the drawings. The features mentioned in the claims and the description and represented in the drawings can be essential to the invention, either individually or in arbitrary combinations.

BRIEF DESCRIPTION OF THE DRAWINGS

FIG. 1: is a top view of a ventral intervertebral implant;

FIG. 2: is a side view of the intervertebral implant of FIG. 1;

FIG. 3: is a section III—III in accordance with FIG. 2;

FIG. 3a: is a section through a holding device for the anchor bolts;

FIG. 4: is a section IV—IV in accordance with FIG. 3, with retractably disposed anchor pins;

FIG. 5: is a section IV—IV in accordance with FIG. 3, with extended anchor pins;

FIG. 6: is a front view of the camshaft of FIG. 4;

FIG. 7: is a section VII—VII through the camshaft, in accordance with FIG. 5;

FIG. 9: is a cross-section through a third embodiment of a camshaft; and

DETAILED DESCRIPTION OF THE PREFERRED EMBODIMENTS

Figure 10:
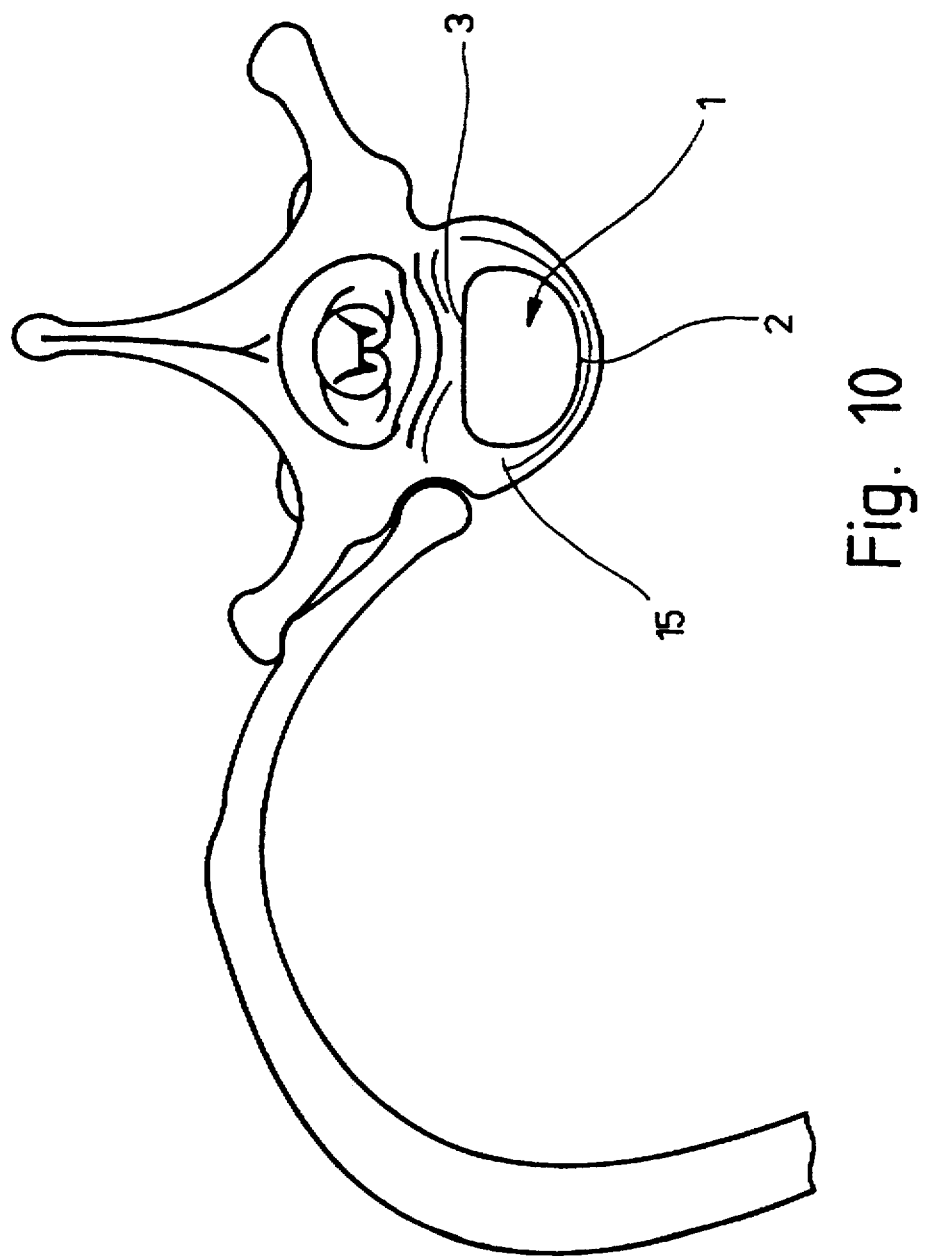
FIG. 10: is a schematic representation of a vertebrae thoracicae with an intervertebral implant resting on it.

FIG. 1 shows a ventral intervertebral implant, indicated in its entirety with 1, which has a cross-sectional shape approaching that of the cross-section of a vertebral body, which can be seen clearly from FIG. 10. Correspondingly, the ventral side 2 of the intervertebral implant 1 is embodied to be convex, whereas the dorsal side 3 is embodied to be flat. It is also conceivable that this dorsal side 3 is concavely curved. Elongated openings 4 and 5, which permit connective tissue and bone tissue to grow into the implant 1, can be seen between these two sides 2 and 3. Further visible are two recesses 6 and 7, in which anchor pins 8 (FIGS. 4 and 5) are seated. Finally, recesses 9 and 10, which discharge from the implant 1 on the opposite contact surface 11, are indicated. The recesses 6 and 7 and 9 and 10 are located in one plane. It can also be seen that the contact surface 12 and the contact surface 11 (FIG. 2) have a profiled surface that is embodied in the manner of sawteeth. In this case, the sawteeth 13 of the contact surface 12 for the implant 1 blocks in the ventral direction, and the sawteeth 14 of the contact surface 11 for the implant 1 blocks in the dorsal direction. These sawteeth 13 and 14 prevent the intervertebral implant 1 from slipping on or between the vertebral bodies 15 resting on them (FIG. 10).

A further opening 16 in which connecting tissue and bone tissue is permitted to grow is visible in the side view of the intervertebral implant 1 shown in FIG. 2. Moreover, the wedge-shaped embodiment is identifiable, and the wedge angle α is between 2° and 15°. The thickness of the implant 1 is 5 mm on the ventral side 2, and 8 mm on the dorsal side.

It can be seen from section III—III shown in FIG. 3 that a bore 17 is located between the two openings 4 and 5 that acts as a seat for a camshaft indicated in its entirety by 18. This camshaft 18 forms the gear for the anchor pins 8, particularly for their displacement from the resting position shown in FIG. 4 into the operating position shown in FIG. 5.

The camshaft 18 has three collars 19 through 21, by means of which it is seated. Two cams 22 and 23 are located between the collars 19 and 20, and two cams 24 and 25 are located between the collars 20 and 21. The collars 19 through 21 project radially beyond the cams 22 through 25, so that a free space always remains between the surfaces of the cams 22 through 25 and the bore wall 17. Furthermore, an interior thread 26 provided in the collar 21 is indicated in FIG. 3, into which a tool 30, having a threaded bolt 32, can be screwed and used to turn the camshaft 18. The tool 30 can have a handle, not shown, for easy gripping. The interior thread 26 is slightly eccentric, and particularly coaxially in respect to the cam 25, so that no unnecessary wall weakening occurs.

Following fixation of the implant 1, the camshaft 18 can be removed by means of the tool 30 and exchanged for a device 29, which maintains the anchor bolts 8 in the work position. This device 29 illustrated in FIG. 3a also has a thread 126 and is provided with a minimal radial protrusion 31 (shown exaggerated in the drawings) which assures clamping of the insert 29 in the implant 1. Thus, the camshaft 18 and the tool 30 constitute one instrument, so that the camshaft 18 can be used several times.

The camshaft 18 is shown in section in FIG. 4, and the anchor pins 8 are shown in their resting position, that is, in their retracted position. In this instance the proximal ends 27 rest on the cams 22 through 25, and the distal ends 28 project slightly beyond the contact surfaces 11 and 12, that is, only so far that problem-free insertion of the intervertebral implant between two vertebral bodies 15 is possible.

FIG. 5 shows the anchor pins 8 in the extended position, and the camshaft 18 assumes a position rotated by 180°. It can further be seen that the proximal ends 27 of the anchor pins 8 rest flush with the bore wall 17.

The displaced position of the interior thread 26 can also be seen clearly from FIG. 6, which shows a front view of the camshaft 18 of FIG. 4. A section VII—VII through the camshaft 18, in accordance with FIG. 5, is shown in FIG. 7, in which the two cams 24 and 25 can be seen. In this embodiment of the camshaft 18, the stroke of the cam is attained by means of one rotation of the camshaft by 180°, so that the regulating distance extends over 180°. It is likewise recognizable from FIG. 7 that the two cams 24 and 25 have an angular offset of 180°, so that anchor pins 8, located opposite one another and penetrating through the two contact surfaces 11 and 12, are pushed out at the same time.

Figure 8:
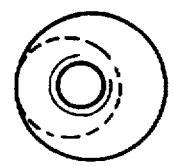
FIG. 8: is a cross-section through a further embodiment of a camshaft.

In the exemplary embodiment of a camshaft 18 shown in FIG. 8, the regulating distance of the cam likewise extends over 180°, but only a single cam is required to extend the anchor pins 8 located opposite one another, so that twice the number of anchor pins 8 can be moved. This cam has a preset direction of rotation. The camshaft, therefore, also has a rotational stop, which is not shown in the drawings.

FIG. 9 shows a further embodiment of a cam that has a regulating distance extending over 360°. With cams embodied in this manner, long displacement distances can be attained with small displacement forces. This cam also has a defined direction of rotation, and the camshaft therefore also has a rotational stop.

What is claimed is:

1. A ventral intervertebral implant for use between two vertebral bodies of a spinal column, comprising: a ventral intervertebral body having an upper and lower contact surface, at least one opening extending generally perpendicular to said contact surfaces, and a further opening extending generally parallel to said contact surfaces and situated to intersect said at least one opening; an anchor pin situated in each opening that extends generally perpendicular to said contact surfaces and projecting beyond at least one of said contact surfaces, each anchor pin being retractably disposed in its respective opening; and a camshaft situated in said further opening for extending each anchor pin into a work position, wherein said camshaft is removable from said further opening after each anchor pin is situated in its work position.

2. The ventral intervertebral implant as defined by claim 1, wherein said camshaft has at least one cam that pushes out a respective anchor pin.

3. The ventral intervertebral implant as defined by claim 1, wherein a plurality of anchor pins are provided, and wherein said plurality of anchor pins can be pushed out via a respective one of a plurality of rotatably seated cams.

4. The ventral intervertebral implant as defined by claim 3, wherein said plurality of rotatably seated cams are disposed axially one behind the other.

5. The ventral intervertebral implant as defined by claim 4, wherein at least one disk-shaped collar that projects beyond said plurality of rotatably seated cams is provided between any two adjacent ones of said rotatably seated cams.

6. The ventral intervertebral implant as defined by claim 5, wherein said disk-shaped collar forms a seating position of said camshaft.

7. The ventral intervertebral implant as defined by claim 1, wherein said camshaft is ventrally accessible.

8. The ventral intervertebral implant as defined by claim 1, wherein said camshaft can be rotated by a tool.

9. The ventral intervertebral implant as defined by claim 1, wherein one face end of said camshaft has an interior thread for a corresponding tool-application device.

10. The ventral intervertebral implant as defined by claim 3, wherein the regulating distance of said rotatably seated cams extends over one of 90°, 180°, and 360°.

11. The ventral intervertebral implant as defined by claim 3, wherein each of said rotatably seated cams is provided with two regulating distances respectively extending over 180°.

12. The ventral intervertebral implant as defined by claim 1, wherein said camshaft has a rotational stop.

13. The ventral intervertebral implant as defined by claim 1, wherein each anchor pin has a cylindrical cross-section and is seated in a corresponding opening in the implant.

14. The ventral intervertebral implant as defined by claim 1, wherein the implant is embodied to be wedge-shaped, and said contact surfaces form a wedge angle ($\alpha$) of 2° to 15°.

15. The ventral intervertebral implant as defined by claim 1, wherein the implant has a thickness of 5 mm to 14 mm, and, with a wedge shape, a thickness of 5 mm to 8 mm or 8 mm to 14 mm.

16. The ventral intervertebral implant as defined by claim 1, wherein at least one of said contact surfaces has a profiled surface.

17. The ventral intervertebral implant as defined by claim 16, wherein each of said two contact surfaces have sawtooth profiles located opposite to one another and which point in different directions.

18. The ventral intervertebral implant as defined by claim 17, wherein the sawtooth profiles point in the ventral direction and the dorsal direction.

19. The ventral intervertebral implant as defined by claim 16, wherein the profiled surface is a toothed surface.

20. The ventral intervertebral implant as defined by claim 1, wherein said camshaft can be threaded on a rod-shaped tool.

21. The ventral intervertebral implant as defined by claim 1, wherein said camshaft can be inserted dorsally or ventrally into the implant.

22. The ventral intervertebral implant as defined by claim 1, further having a device which maintains each anchor pin in a work position.

23. The intervertebral implant as defined by claim 22, wherein said device is releasable.

24. The ventral intervertebral implant as defined by claim 1, wherein the implant is embodied to be wedge-shaped, and said contact surfaces form a wedge angle ($\alpha$) of 3° to 10°.

* * * * *